US012318508B2

(12) United States Patent
Olson et al.

(10) Patent No.: US 12,318,508 B2
(45) Date of Patent: Jun. 3, 2025

(54) COMPOSITIONS FOR TREATMENT OF DISCOGENIC PAIN, AND PROCESSES FOR MAKING AND USING THE SAME

(71) Applicant: 33 Medical, Inc., Boca Raton, FL (US)

(72) Inventors: Eric Olson, Washington, UT (US); Jeff Zisselman, Boca Raton, FL (US); Nick Manesis, Escondido, CA (US); Richard Wesley Sierk, III, Rancho Palos Verdes, CA (US)

(73) Assignee: 33 MEDICAL, INC., Boca Raton, FL (US)

(*) Notice: Subject to any disclaimer, the term of this patent is extended or adjusted under 35 U.S.C. 154(b) by 0 days.

(21) Appl. No.: 18/732,203

(22) Filed: Jun. 3, 2024

(65) Prior Publication Data
US 2024/0399028 A1 Dec. 5, 2024

Related U.S. Application Data

(60) Provisional application No. 63/505,951, filed on Jun. 2, 2023.

(51) Int. Cl.
A61L 27/52 (2006.01)
A61K 49/04 (2006.01)
A61L 27/26 (2006.01)
A61L 27/48 (2006.01)

(52) U.S. Cl.
CPC .......... *A61L 27/52* (2013.01); *A61K 49/0438* (2013.01); *A61L 27/26* (2013.01); *A61L 27/48* (2013.01); *A61L 2300/442* (2013.01); *A61L 2300/802* (2013.01); *A61L 2400/06* (2013.01); *A61L 2430/38* (2013.01)

(58) Field of Classification Search
CPC .... A61L 27/52; A61L 27/16; A61L 2300/442; A61L 2300/802; A61L 2400/06; A61L 2430/38; A61K 9/0085; A61K 9/06; A61K 9/1635; A61K 47/18; A61K 47/32; A61K 47/34
See application file for complete search history.

(56) References Cited

U.S. PATENT DOCUMENTS

| | | | |
|---|---|---|---|
| 2,474,911 A | 7/1949 | Pierce et al. | |
| 4,526,909 A | 7/1985 | Urist | |
| 4,580,440 A | 4/1986 | Reid et al. | |
| 4,837,285 A | 6/1989 | Berg et al. | |
| 5,024,659 A | 6/1991 | Sjostrom | |
| 5,134,122 A | 7/1992 | Orsolini | |
| 5,171,279 A | 12/1992 | Matthews | |
| 5,258,028 A | 11/1993 | Ersek et al. | |
| 5,286,763 A | 2/1994 | Gerhart et al. | |
| 5,290,271 A | 3/1994 | Jernberg | |
| 5,344,452 A | 9/1994 | Lemperle | |
| 5,352,715 A | 10/1994 | Wallace et al. | |
| 5,571,182 A | 11/1996 | Ersek et al. | |
| 5,599,852 A | 2/1997 | Scopelianos et al. | |
| 5,641,514 A | 6/1997 | Cho | |
| 5,922,025 A | 7/1999 | Hubbard | |
| 6,107,466 A | 8/2000 | Hasan et al. | |
| 6,129,761 A | 10/2000 | Hubbell | |
| 6,160,033 A | 12/2000 | Nies | |
| 6,183,518 B1 | 2/2001 | Ross et al. | |
| 6,264,650 B1 | 7/2001 | Hovda et al. | |
| 6,264,651 B1 | 7/2001 | Underwood et al. | |
| 6,264,659 B1 | 7/2001 | Ross et al. | |
| 6,264,695 B1 | 7/2001 | Stoy | |
| 6,284,872 B1 | 9/2001 | Celeste et al. | |
| 6,309,420 B1 | 10/2001 | Preissman | |
| 6,335,028 B1 | 1/2002 | Vogel et al. | |
| 6,355,705 B1 | 3/2002 | Bond et al. | |
| 6,383,200 B1 | 5/2002 | Wotton | |
| 6,391,059 B1 | 5/2002 | Lemperle et al. | |
| 6,432,437 B1 | 8/2002 | Hubbard | |
| 6,468,274 B1 | 10/2002 | Alleyne et al. | |
| 6,500,180 B1 | 12/2002 | Foley et al. | |
| 6,602,248 B1 | 8/2003 | Sharps et al. | |
| 6,652,883 B2 | 11/2003 | Goupil et al. | |
| 6,713,527 B2 | 3/2004 | Bond et al. | |
| 7,060,103 B2 | 6/2006 | Carr et al. | |

(Continued)

FOREIGN PATENT DOCUMENTS

| CA | 2578113 A1 | 3/2006 |
|---|---|---|
| CA | 2703807 | 11/2011 |

(Continued)

OTHER PUBLICATIONS

Extended European Search Report dated Apr. 20, 2017 in European Patent Application No. 16738015.3.
JPO Notice of Rejection dated Dec. 7, 2021 in Japanese Patent Application No. 2021-005260.
Office Action mailed Dec. 13, 2021 by the Canadian Intellectual Property Office in Patent Application No. 2973727.
Technical Opinion of the Brazilian Patent Office, mailed Oct. 8, 2021, in Patent Application No. BR112017015095-6.
Wang, Ying et al., "Combination of Hyaluronic Acid Hydrogel Scaffold and PLGA Microspheres for Supporting Survival of Neural Stem Cells," Pharmaceutical Research, 28, May 4, 2011 (Apr. 5, 2011).

(Continued)

*Primary Examiner* — Robert S Cabral
(74) *Attorney, Agent, or Firm* — Husch Blackwell LLP; Andrew C. Landsman; Bryan D. Stewart

(57) ABSTRACT

Compositions for treatment of discogenic pain are discussed herein. In various embodiments, the composition includes PMMA microparticles, Pluronic® surfactant, PBS, and a radio marker. In some embodiments, the PMMA microparticles have a particle size distribution between 25-125 microns and are nonlinearly cross-linked. The composition may be stored at a cooled temperature and upon injection, the composition warms and transitions to a gel state. The composition may also include about 50% PMMA microparticles, about 10% Pluronic®, about 30% PBS, and about 10% of a radio marker.

26 Claims, 5 Drawing Sheets

(56) References Cited

U.S. PATENT DOCUMENTS

| | | |
|---|---|---|
| 7,131,997 B2 | 11/2006 | Bourne et al. |
| 7,306,627 B2 | 12/2007 | Tanagho et al. |
| 7,341,601 B2 | 3/2008 | Eisermann et al. |
| 7,442,389 B2 | 10/2008 | Quelle et al. |
| RE41,286 E | 4/2010 | Atkinson et al. |
| 8,127,770 B2 | 3/2012 | Alleyne et al. |
| 8,357,795 B2 | 1/2013 | Lebreton |
| 8,398,638 B2 | 3/2013 | Alleyne et al. |
| 8,586,089 B2 | 11/2013 | Anderson |
| 8,951,255 B2 | 2/2015 | Alleyne et al. |
| 9,351,769 B2 | 5/2016 | Alleyne et al. |
| 10,279,080 B2 | 5/2019 | Young et al. |
| 10,806,825 B2 | 10/2020 | Young et al. |
| 11,607,475 B2 | 3/2023 | Young et al. |
| 12,156,956 B2 | 12/2024 | Young et al. |
| 2002/0045942 A1 | 4/2002 | Ham |
| 2002/0120259 A1 | 8/2002 | Lettice |
| 2002/0176893 A1 | 11/2002 | Wironen et al. |
| 2003/0009235 A1 | 1/2003 | Manrique et al. |
| 2003/0014051 A1 | 1/2003 | Woloszko |
| 2003/0040742 A1 | 2/2003 | Underwood et al. |
| 2003/0149490 A1 | 8/2003 | Ashman |
| 2003/0158545 A1 | 8/2003 | Hovda et al. |
| 2003/0158607 A1 | 8/2003 | Carr et al. |
| 2003/0211083 A1 | 11/2003 | Vogel et al. |
| 2003/0212395 A1 | 11/2003 | Woloszko et al. |
| 2003/0236573 A1 | 12/2003 | Evans et al. |
| 2004/0010317 A1 | 1/2004 | Lambrecht et al. |
| 2004/0024465 A1 | 2/2004 | Lambrecht et al. |
| 2004/0054414 A1 | 3/2004 | Trieu et al. |
| 2004/0091540 A1 | 5/2004 | DesRosiers et al. |
| 2004/0115240 A1 | 6/2004 | Narhi et al. |
| 2004/0127963 A1 | 7/2004 | Uchida et al. |
| 2005/0031666 A1 | 2/2005 | Trieu |
| 2005/0100510 A1 | 5/2005 | Falco |
| 2006/0002971 A1 | 1/2006 | Saltzman et al. |
| 2006/0052795 A1 | 3/2006 | White |
| 2006/0074424 A1 | 4/2006 | Alleyne et al. |
| 2006/0093644 A1 | 5/2006 | Qiuelle et al. |
| 2006/0206116 A1 | 9/2006 | Yeung |
| 2006/0263830 A1 | 11/2006 | Grinstaff et al. |
| 2007/0093907 A1 | 4/2007 | Goupil et al. |
| 2007/0168038 A1 | 7/2007 | Trieu |
| 2008/0096976 A1 | 4/2008 | Alleyne et al. |
| 2008/0107744 A1* | 5/2008 | Chu ............... A61K 9/0031 514/789 |
| 2008/0124371 A1 | 5/2008 | Turos et al. |
| 2008/0160060 A1 | 7/2008 | Ellies |
| 2008/0166386 A1 | 7/2008 | Caseres et al. |
| 2008/0299172 A1 | 12/2008 | Young et al. |
| 2009/0074728 A1 | 3/2009 | Gronthos et al. |
| 2010/0004699 A1 | 1/2010 | Alleyne et al. |
| 2010/0004700 A1 | 1/2010 | Alleyne |
| 2010/0010549 A1 | 1/2010 | Alleyne et al. |
| 2010/0028438 A1 | 2/2010 | Lebreton |
| 2010/0041788 A1 | 2/2010 | Voigts et al. |
| 2010/0172829 A1 | 7/2010 | Anderson |
| 2010/0316715 A1 | 12/2010 | Anderson |
| 2011/0230919 A1 | 9/2011 | Alleyne |
| 2012/0310140 A1 | 12/2012 | Kramer et al. |
| 2017/0296701 A1 | 10/2017 | Young et al. |
| 2020/0188660 A1 | 6/2020 | Franke et al. |
| 2020/0345896 A1 | 11/2020 | Peyman |
| 2022/0218878 A1 | 7/2022 | Rai et al. |

FOREIGN PATENT DOCUMENTS

| | | |
|---|---|---|
| CN | 1852743 A | 10/2006 |
| CN | 101502676 A | 8/2009 |
| CN | 101426451 B | 6/2011 |
| CN | 101502676 B | 2/2013 |
| EP | 1410810 B1 | 1/2007 |
| JP | 6508795 B2 | 12/1993 |
| JP | 2002505308 A | 2/2002 |
| JP | 2008509935 A | 4/2008 |
| JP | 2008511420 A | 4/2008 |
| JP | 2011525493 A | 9/2011 |
| KR | 1020090043973 A | 5/2009 |
| WO | 1992010982 A1 | 7/1992 |
| WO | 1998040113 A1 | 9/1998 |
| WO | 1999044643 A1 | 9/1999 |
| WO | 2000044394 A1 | 8/2000 |
| WO | 2000044808 A1 | 8/2000 |
| WO | 2001068721 A1 | 9/2001 |
| WO | 2002040070 A2 | 5/2002 |
| WO | 2002062404 A3 | 6/2003 |
| WO | 2003049669 A2 | 6/2003 |
| WO | 2005046746 A2 | 5/2005 |
| WO | 2004026189 A3 | 12/2007 |
| WO | 2008005676 A2 | 1/2008 |
| WO | 2009155656 A1 | 12/2009 |
| WO | 2010015901 | 2/2010 |
| WO | 2013006671 | 1/2013 |

OTHER PUBLICATIONS

Alleman et al. "Hyaluronic acid gel (Juvederm) preparations ii the treatment of facial wrinkles and folds" Clinical Interventions in Aging 2008:3(4) 629-634.

Bayston, et al. "The sustained release of antimicrobial drugs from bone cement. An appraisal of laboratory investigations and their significance," J. Bone Joint Surg. (Br), (1982) 62(4): 460-464.

Bergeret-Galley et al. The Value of a New Filler Material in Corrective and Cometic Surery: Derrnalive and DermaDeep (Aesthetic Plastic Surgery; 2001; 25: 249-255) (Year: 2001).

Carruthers, Artecoll—"An injectable micro-implant for longlasting soft tissue augmentation," Skin Therapy Letter, (1999), vol. 4(2), 1-2.

Cohen et al., Artecoll—A Long-Lasting Injectable Wrinkle Filler Material: Report of a Controlled, Randomized, Multicenter Clinical Trial of 251 Subjects, Plastic Reconst. Surg., (2004) vol. 114(4), 964-976.

Comparison chart [online] retreived on Apr. 25, 18 from http://tru-flo.com/Technical/viscosity_chart.pdf; 1 page (Year 2018).

English Abstract to CN 101502676A Aug. 12, 2009; 2 pages. (Year 2009).

English translation of CN101502676B (published Aug. 12, 2009) 16 pages. (Year 2009).

Examination Report No. 1 for Australian standard patent application 2016206507, May 11, 2020, Sydney, Australia.

Faught, W.E. and Lawrence, P.F. "The effects of laser energy on the arterial wall." Annals of Vascular Surgery 4 (1990); 198-207.

PDA Approval Document for JuvederM—2006.

Goisis, M., (Injections in Aesthetic Medicine: Atlas of Full-face and Full-body Treatment 2013; Springer Science & Business Media, pp. 279-280) (Year: 2013).

Goisis, M., (Injections in Aesthetic Medicine: Atlas of Full-face and Full-body Treatment; Springer Science & Business Media, pp. 279-280) (Year: 2014).

Hoffman, K "Volumizing effects of a smooth, highly cohesive, viscous 20-mg/mL hyaluronic acid volumizing filler: prospective European study." (BMC Dermatology 2009; 9: p. 1-9) (Year: 2009).

Hu et al.Acta Polymerica Sinica 2003; 540-545 (Year: 2003).

International Search Report mailed Jun. 22, 2016 in International Application No. PCT/US2016/013718.

Kablik et al. (Dermatol Surg 2009; 35:302-312). (Year: 2009).

Kim et al. Effect of Crosslinking Agents on the Morphology of Polymer Particles Produced by One-Step Seeded Polymerization (Macromolecular Research 2009; 17(4): 250258) (Year: 2009).

KIPO Notice of Preliminary Rejection dated Nov. 9, 2018 in KR Patent Application No. 10-2017-7022753.

Lautenschlager, "Hyaluronic Acid—A Legendary Agent" Kosmetische Praxis 2008 (4), 16-18.

Lemperle et al. "Permanent Injectable for Soft Tissue Augmentation: I. Mechanism of Action and Injection Techniques." (Aesth Plast Surg 2010; 34:264-272). (Year: 2010).

(56) References Cited

OTHER PUBLICATIONS

Liga et al. "Safe and cost-effective rapid-prototyping of multilayer PMMA microfluidic devices." (Microfluid Nanofluid 2016; 20(164): 12 pages) (Year 2016).
Masala, et al., "Percutaneous Vertebroplasty in Painful Schmorl Nodes," Published Online Nov. 18, 2005, Cardiovasc Intervent Radiol 29:97-101.
Omlor, G.W. el. al., Injection of a polymerized hyaluronic acid/ collagen hydrogel matrix in an in vivo porcine disc degeneration model. European Spine Journal, 2012, vol. 21, pp. 1700-1708.
Rodrigues et al. (J Biomed Mater Res Part B: Appl Biomater 92B: 2010 pp. 13-23) (Year: 2010).
Sundaram et al., "Comparision of the Rheological Properties of Viscosity and Elasticity in Two Categories of Soft Tissue Fillers: Calcium Hydroxylapatite and Hyaluronic Acid" Dermatol Surg 201 0; 36: 1 1859-1865.
Viscosity comparison chart [online] retrieved on Jul. 4, 2018 from: http://www.cstsales.com/viscosity.html; 1 page (Year 2018).
Wahlig, et al., "Pharmacokinetic study of gentamicin-loaded cement in total hip replacements. Comparative effects of varying dosage." J Bone Joint Surg. (Br), (1984) 66(2): 175-179.
Baumann et al. (Journal of Controlled Release 2009; 138:205/213). (Year: 2009).
International Search Report & Written Opinion mailed Oct. 17, 2024 for Intl Pat. Appl. No. PCT/US24/32275.

\* cited by examiner

COMPOSITIONS FOR TREATMENT OF DISCOGENIC PAIN, AND PROCESSES FOR MAKING AND USING THE SAME

TECHNICAL FIELD

The present disclosure relates generally to compositions of surgical implants and formulations, and, more particularly, relates to injectable compositions and methods of use.

BACKGROUND

Spinal disks comprise a central region called the nucleus pulposus surrounded by a second region known as the annulus fibrosis. The annulus fibrosis portion comprises collagen fibers that may weaken, rupture, or tear, leading to compromised annular confinement of the nucleus and producing disk bulges, herniations and other disk pathologies. The major causes of persistent, often disabling, back pain may include disruption of the spinal disk annulus fibrosis, chronic inflammation of the spinal disk (e.g., herniation), or relative instability of the vertebral bodies surrounding a given spinal disk, such as the instability that often occurs due to a degenerative disease. In some cases, the spinal disk tissue is irreparably damaged, thereby necessitating surgical removal of a portion of the spinal disk or the entire spinal disk to eliminate the source of inflammation and pressure. Following removal, spinal disks may contain annular defects or openings that can increase the possibility of recurrent complications such as, for example, future nuclear herniations.

Some methods to treat such defects focus on injecting compositions containing collagen based suspending agents into an affected spinal disk. Additional methods include injecting compositions including microparticles suspended in a collagen suspending agent in order to treat a damaged spinal disk. Furthermore, various methods include injections of composition of microparticles and a biocompatible carrier medium in the form of cross-linked collagen and biocompatible gelatin. However, a major issue with the currently used injectable compositions for the treatment of a damaged spinal disk include the leakage of the composition out of the nucleus pulposus, which may cause ineffective treatment.

As a result, there is a need for compositions for use in treatment of discogenic pain that may treat discogenic pain when injected into nucleus pulposus and wherein the composition does not leak out of the nucleus pulposus.

BRIEF SUMMARY OF THE DISCLOSURE

According to a first aspect, an injectable composition comprising: about 10-90% poly methyl methacrylate (PMMA) microparticles; about 10-90% Pluronic® surfactant; about 15-50% phosphate buffered saline (PBS); and about 5-25% sodium diatrizoate hydrate, wherein the PMMA microparticles have a particle size distribution between about 25-125 microns and are nonlinearly cross-linked.

According to a second aspect, a process comprising: producing a carrier solution by mixing PBS, Pluronic® surfactant, and sodium diatrizoate hydrate in water; producing a therapeutic solution by mixing a plurality of nonlinearly cross-linked PMMA microparticles with a particle size distribution of about 25-125 microns into the carrier solution using a mixer at room temperature for about 2 minutes at 2000 rpm, wherein the therapeutic solution comprises about 10-90% Pluronic® surfactant, about 15-50% PBS, about 5-25% sodium diatrizoate hydrate, and about 10-90% PMMA microparticles; chilling and adding the therapeutic to a syringe vial; inserting a stopper, cap, and/or crimp into the syringe vial; packaging the syringe vial in a pouch; sterilizing the syringe vial via terminal sterilization; and storing the sterilized syringe vial at about 3-8° C.

According to a third aspect, a method of treating discogenic pain comprising: inserting a needle into a nucleus pulposus of a spinal disc of a patient; injecting a therapeutic solution into the nucleus pulposus of the spinal disc, wherein: the therapeutic solution comprises: about 10-90% nonlinearly cross-linked PMMA microparticles with a particle size distribution of about 25-125 microns; about 10-90% Pluronic® surfactant; about 15-50% PBS; and about 5-25% sodium diatrizoate hydrate; after injection, a temperature of the spinal disc causes a temperature of the therapeutic solution to rise, thereby causing the Pluronic® surfactant to gel and provide a bulking effect to the spinal disc.

According to a fourth aspect, a method of treating discogenic pain further comprising after injection, using a stopcock on the syringe and/or a needle stylet in order to allow the composition to remain in the patient until gelling of the composition occurs which prevents back extrusion of the product through the needle, whereby time to gelation is about 3-5 minutes.

According to a fifth aspect, a method of treating discogenic pain wherein injecting the therapeutic solution into the nucleus pulposus of the spinal disc is a first injection; and the method further comprises: determining a pain level of the patient after the first injection; and in response to determining that the pain level of the patient is above a particular threshold, injecting the therapeutic solution into the nucleus pulposus of the spinal disc a second time.

According to a sixth aspect an injectable composition comprising PMMA microparticles wherein the PMMA microparticles have a particle size distribution between about 25-125 microns and are nonlinearly cross linked.

According to a seventh aspect, an injectable composition comprising about 10-90% PMMA microparticles wherein the PMMA microparticles have a particle size distribution between about 25-125 microns and are nonlinearly cross linked and about 10-90% Pluronic® surfactant.

According to an eighth aspect, an injectable composition comprising about 10-90% PMMA microparticles wherein the PMMA microparticles have a particle size distribution between about 25-125 microns and are nonlinearly cross linked, about 10-90% Pluronic® surfactant, and about 15-50% PBS.

According to a ninth aspect, an injectable composition comprising about 10-90% PMMA microparticles wherein the PMMA microparticles have a particle size distribution between about 25-125 microns and are nonlinearly cross linked, about 10-90% Pluronic® surfactant, and about 15-50% PBS, and about 5-25% sodium diatrizoate hydrate.

According to a tenth aspect, a process comprising: producing a carrier solution via mixing PBS, Pluronic® surfactant, and sodium diatrizoate hydrate in water; producing a therapeutic solution via mixing a plurality of nonlinearly cross-linked PMMA microparticles with a particle size distribution of about 25-125 microns into the carrier solution using a mixer at room temperature for about 2 minutes at 2000 rpm, wherein the therapeutic solution comprises about 10-90% Pluronic® surfactant, about 15-50% PBS, about 5-25% sodium diatrizoate hydrate, and about 10-90% PMMA microparticles; chilling and adding the therapeutic to a syringe; and adding a secondary syringe vial; packaging the syringe vial and secondary syringe in a pouch; sterilizing the syringe vial via terminal sterilization; and storing the sterilized syringes at about 3-8 degrees° C.; wherein in advance of injecting the therapeutic composition into the patient via a spinal needle, the two syringes are connected via a coupler; wherein the composition is exchanged between the two syringes several times, in order to mix the composition.

According to an eleventh aspect, a method of treating discogenic pain comprising: the injecting a therapeutic composition; wherein: the therapeutic solution comprises: about 10-90% nonlinearly cross-linked PMMA microparticles with a particle size distribution of about 25-125 microns; about 10-90% Pluronic® surfactant; about 15-50% PBS; and about 5-25% sodium diatrizoate hydrate; in combination with a radiopaque dye, wherein said dye provides accurate visualization of the material in the spinal disc during injection and subsequent gelling of the hydrogel, wherein; said dye will also allow for visualization to ensure that the therapeutic composition will not extrude through the annulus of the disc.

According to a twelfth aspect, an injectable composition comprising: about 35-55% PMMA microparticles; about 8-12% Pluronic® surfactant; about 19-42% PBS; and about 8-14% sodium diatrizoate hydrate, wherein the PMMA microparticles have a particle size distribution between about 53-106 microns and are nonlinearly cross-linked.

According to a thirteenth aspect, a process as further comprising: producing a carrier solution by mixing PBS, Pluronic® surfactant, and sodium diatrizoate hydrate in water; producing a therapeutic solution by mixing a plurality of nonlinearly cross-linked PMMA microparticles with a particle size distribution of about 53-106 microns into the carrier solution using a mixer at room temperature for about 2 minutes at 2000 rpm, wherein the therapeutic solution comprises about 8-10% Pluronic® surfactant, about 42-45% PBS, about 9-12% sodium diatrizoate hydrate, and about 35-40% PMMA microparticles; chilling and adding the therapeutic to a syringe vial; inserting a stopper, cap, and/or crimp into the syringe vial; packaging the syringe vial in a pouch; sterilizing the syringe vial via terminal sterilization; and storing the sterilized syringe vial at about 3-8 degrees° C.

According to fourteenth aspect, a method of treating discogenic pain wherein the therapeutic solution further comprises: about 35-40% nonlinearly cross-linked PMMA microparticles with a particle size distribution of about 53-106 microns; about 8-10% Pluronic® surfactant; about 42-45% PBS; and about 9-12% sodium diatrizoate hydrate.

According to a fifteenth aspect, a composition of matter comprising about 30-60% poly (methyl methacrylate) (PMMA) microparticles, about 8-25% Pluronic® surfactant, about 19-49% phosphate buffered saline (PBS), and about 8-14% of a radio marker, wherein the PMMA microparticles have a particle size distribution between about 25-125 microns and are nonlinearly cross-linked.

According to a sixteenth aspect, the composition according to the fifteenth aspect wherein the composition further comprises about 35-55% PMMA and about 8-12% Pluronic® surfactant.

According to a seventeenth aspect the composition according to the fifteenth aspect wherein the PMMA microparticles have a particle size distribution between about 53-106 microns and are nonlinearly cross-linked.

According to an eighteenth aspect, the composition according to the fifteenth aspect wherein the composition further comprises about 2-3% carboxymethylcellulose.

According to a nineteenth aspect, the composition according to the fifteenth aspect wherein the composition is a liquid at temperatures of about 3-8° C. and a gel at body temperature.

According to a twentieth aspect, the composition according to the nineteenth aspect wherein the composition has a time to gelation from about 3-8° C. to body temperature of about 30 seconds to 20 minutes.

According to a twenty first aspect, the composition according to the twentieth aspect wherein the composition has a time to gelation from about 3-8° C. to body temperature of about 2 minutes to 15 minutes.

According to a twenty second aspect, the composition according to the twenty first aspect wherein the composition has a time to gelation from about 3-8° C. to body temperature of about 3 minutes to 5 minutes.

According to a twenty third aspect, the composition according to the twentieth aspect wherein the composition has a time to gelation from about 3-8° C. to body temperature of about 30 seconds to 5 minutes.

According to a twenty fourth aspect, the composition according to the fifteenth aspect wherein the composition has a pre-injection viscosity of about 68400 cP to about 72000 cP.

According to a twenty fifth aspect, a method of making a composition of matter, wherein the composition comprises about 8-25% Pluronic® surfactant, about 19-49% PBS, about 8-14% of the radio marker, and about 30-60% PMMA microparticles, the method comprising the steps of: mixing PBS, Pluronic® surfactant, and a radio marker to form a carrier solution, mixing a plurality of nonlinearly cross-linked PMMA microparticles, wherein the PMMA microparticles have a particle size distribution of about 25-125 microns, into the carrier solution, chilling the composition to about 3-8° C., adding the composition to a vial, sealing the vial, sterilizing the vial, and storing the sterilized vial at about 3-8° C.

According to a twenty sixth aspect, the method of the twenty fifth aspect wherein the mixing of the PMMA microparticles is performed using a mixer at room temperature for about 2 minutes at about 2000 rpm.

According to a twenty seventh aspect, the method of the twenty fifth aspect wherein the vial is sealed by one of inserting a stopper, cap, or crimp into the vial.

According to a twenty eighth aspect, the method of the twenty fifth aspect wherein the vial is sterilized using terminal sterilization.

According to a twenty-ninth aspect, the method of the twenty fifth aspect wherein the mixing of the PMMA microparticles into the carrier solution occurs at about 20° C.

According to a thirtieth aspect, the method of the twenty fifth aspect wherein the radio marker comprises radiopaque dye.

According to a thirty first aspect, a method of treating discogenic pain comprising the steps of: inserting a needle into a nucleus pulposus of a spinal disc of a patient, the needle attached to a syringe containing a composition in a liquid state, the composition comprising; about 30-60% nonlinearly cross-linked PMMA microparticles with a particle size distribution of about 25-125 microns, about 8-25% Pluronic® surfactant, about 19-49% PBS, and about 8-14% of a radio marker; injecting the composition in a liquid state into the nucleus pulposus of the spinal disc; after injecting the composition into the nucleus pulposus, waiting until the composition transitions to a gel and provides a bulking effect to the spinal disc; and removing the needle from the patient.

According to a thirty second aspect, the method of the thirty first aspect further comprising the step of, after injection, closing a stopcock on the syringe while the composition transitions to a gel to prevent back extrusion of the composition through the needle.

According to a thirty third aspect, the method of the thirty first aspect wherein injecting the composition into the nucleus pulposus of the spinal disc is a first injection; and the method further comprises the steps of: determining a pain level of the patient after the first injection, and in response to determining that the pain level of the patient is above a particular threshold, injecting the therapeutic solution into the nucleus pulposus of the spinal disc a second time.

According to a thirty fourth aspect, a method of producing a composition of matter comprising the steps of: making a carrier solution by mixing PBS, Pluronic® surfactant, and sodium diatrizoate hydrate, making a solution by mixing a plurality of nonlinearly cross-linked PMMA microparticles with a particle size distribution of about 25-125 microns into the carrier solution, wherein the therapeutic solution comprises about 8-25% Pluronic® surfactant, about 19-49% PBS, about 5-25% sodium diatrizoate hydrate, and about 30-60% PMMA microparticles; chilling and adding a first portion of the composition of matter to a first syringe vial; adding a second portion of the composition of matter to a second syringe vial; packaging the first syringe vial and second syringe in a pouch; sterilizing the first and second syringe vials via terminal sterilization; and storing the sterilized first and second syringes at about 3-8° C.; wherein in advance of injecting the therapeutic composition into the patient via a spinal needle, the first and second syringes are connected via a coupler; wherein the composition is exchanged between the two syringes several times, in order to mix the composition.

According to a thirty fifth aspect, a method of treating discogenic pain comprising the steps of: storing, at about 3-8° C., a vial having a cap, wherein the vial contains a composition, the composition comprising: about 30-60% poly (methyl methacrylate) (PMMA) microparticles; about 8-25% Pluronic® surfactant; about 19-49% phosphate buffered saline (PBS); and about 8-14% of a radio marker, wherein the PMMA microparticles have a particle size distribution between about 25-125 microns and are nonlinearly cross-linked; removing the vial from storage; shaking the vial to mix the composition; removing the cap from the vial; attaching a cannula onto a syringe, the syringe having a plunger; inserting the cannula into the vial; withdrawing the composition from the vial into the syringe; attaching a spinal needle to the syringe, the spinal needle including a stopcock, wherein the stopcock is in an open position when it is attached to the syringe; remove any entrapped air from the spinal needle by ejecting a small amount of the composition from the syringe through the spinal needle; inserting the spinal needle into an intervertebral disc of a patient; injecting the composition into the intervertebral disc of the patient; upon fully injecting the composition into the intervertebral disc of the patient, moving the stopcock to a closed position; removing the syringe from the stopcock; allowing the composition to transition from a liquid to a gel as the composition increases in temperature; and upon gelation of the composition within the intervertebral disc of the patient, remove the spinal needle from the patient.

According to a thirty sixth aspect, the method of the thirty fifth aspect wherein the composition further comprises about 35-55% PMMA and about 8-12% Pluronic® surfactant.

According to a thirty seventh aspect, the method of the thirty fifth aspect wherein the PMMA microparticles have a particle size distribution between about 53-106 microns and are nonlinearly cross-linked.

According to a thirty eighth aspect, the method of the thirty fifth aspect wherein the composition further comprises about 2-3% carboxymethylcellulose.

According to a thirty ninth aspect, the method of the thirty fifth aspect wherein the composition is a liquid at temperatures of about 3-8° C. and a gel at body temperature.

According to a fortieth aspect, the method of the thirty fifth aspect wherein the composition has a time to gelation from about 3-8° C. to body temperature of about 30 seconds to 20 minutes.

According to a forty first aspect, a method of treating discogenic pain comprising the steps of: storing, at about 3-8° C., a vial having a cap and a septum, wherein the vial contains a composition, the composition comprising: about 30-60% poly (methyl methacrylate) (PMMA) microparticles; about 8-25% Pluronic® surfactant; about 19-49% phosphate buffered saline (PBS); and about 8-14% of a radio marker, wherein the PMMA microparticles have a particle size distribution between about 25-125 microns and are nonlinearly cross-linked; removing the vial from storage; removing the cap from the vial; affixing a first needle to a luer lock of a 5 mL syringe; inserting the first needle through the septum of the vial so that the needle enters the vial; mixing the composition in the vial; withdrawing the composition from the vial into the 5 mL syringe; replacing the first needle with a spinal needle by removing the first needle from the luer lock and attaching the spinal needle to the luer lock; ejecting a small amount of the composition through the spinal needle to remove any entrapped air from the needle; inserting the spinal needle into an intervertebral disc of a patient; injecting a desired volume of the composition through the spinal needle into the intervertebral disc of the patient; allowing the composition to transition from a liquid to a gel as the composition increases in temperature; and upon gelation of the composition within the intervertebral disc of the patient, remove the spinal needle from the patient.

According to a forty second aspect, the method of the forty first aspect wherein the composition further comprises about 35-55% PMMA and about 8-12% Pluronic® surfactant.

According to a forty third aspect, the method of the forty first aspect wherein the PMMA microparticles have a particle size distribution between about 53-106 microns and are nonlinearly cross-linked.

According to a forty fourth aspect, the method of the forty first aspect wherein the composition further comprises about 2-3% carboxymethylcellulose.

According to a forty fifth aspect, the method of the forty first aspect wherein the composition is a liquid at temperatures of about 3-8° C. and a gel at body temperature.

According to a forty sixth aspect, the method of the forty first aspect wherein the composition has a time to gelation from about 3-8° C. to body temperature of about 30 seconds to 20 minutes.

DETAILED DESCRIPTION

Figure 1:
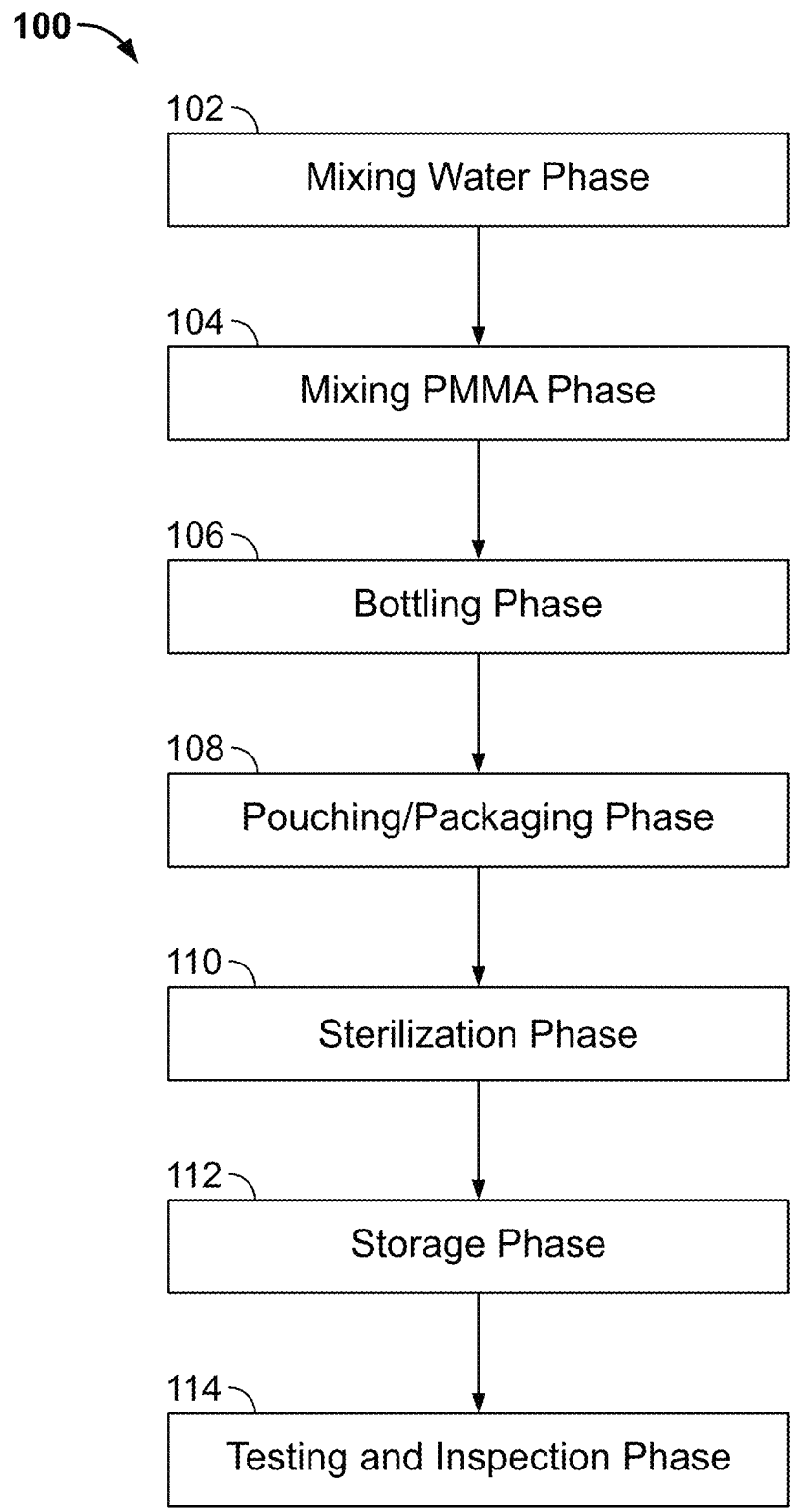
FIG. 1 is an exemplary process for making a composition for treatment of discogenic pain, according to one embodiment.

Whether or not a term is capitalized is not considered definitive or limiting the meaning of a term. As used in this document, a capitalized term shall have the same meaning as an uncapitalized term is intended. However, the capitalization or lack thereof within the remainder of this document is not intended to be necessarily limiting unless the context clearly indicates that such limitation is intended.

Before any embodiments are described in detail, it is to be understood that the disclosure is not limited in its application to the details of construction and the arrangement of components set forth in the following description or illustrated in the following drawings, which is limited only by the claims that follow the present disclosure. The disclosure is capable of other embodiments, and of being practiced, or of being carried out, in various ways. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following description is presented to enable a person skilled in the art to make and use embodiments of the disclosure. Various modifications to the illustrated embodiments will be readily apparent to those skilled in the art, and the generic principles herein may be applied to other embodiments and applications without departing from embodiments of the disclosure. Thus, embodiments of the disclosure are not intended to be limited to embodiments shown but are to be accorded the widest scope consistent with the principles and features disclosed herein. The following detailed description is to be read with reference to the figures, in which like elements in different figures have like reference numerals. Skilled artisans will recognize the examples provided herein have many useful alternatives and fall within the scope of embodiments of the disclosure.

To promote an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Overview

The present disclosure generally relates to compositions for treating discogenic pain related to the degeneration of the invertebrate spinal discs that may have tears or fissures on the annulus fibrosus. An aspect of the present disclosure generally relates to a method for producing a composition for treating a spinal disc. In particular, the present disclosure relates to a method for treating invertebrate spinal discs using a composition comprising hydrogel and microparticles that-after the composition is set into a gel state—is supportive and may provide short term bulking, thereby at least partially restoring the height and stability of the disc. The subject matter claimed herein is not limited to embodiments that solve any disadvantages or that operate only in environments such as those described above. Rather, this background is only provided to illustrate one example technology area where some implementations described herein may be practiced.

In particular, this disclosure relates to an injectable composition to treat discogenic pain, as well as related devices and methods. In some embodiments, the injectable compositions may be liquid when cooled to about 3-8° C. and be a gel when warmed to human body temperature. Various features and aspects disclosed herein provide for compositions and instrumentations for spinal procedures, thereby allowing clinicians to inject the composition accurately and safely via fluoroscopic surgical approach.

Exemplary Compositions

In various embodiments, the compositions include biocompatible microparticles. In some embodiments, the composition may include any suitable biocompatible microparticles without departing from the principles of this disclosure.

As used herein, the term "microparticles" refers to microparticles (e.g., in a dust or powder form) possessing an average diameter of 500 microns or less. "Microparticles" may include microspheres or beads. In various embodiments, the composition may include microparticles having an average diameter less than about 500 microns. In some embodiments, the composition may include microparticles having an average diameter less than about 200 microns. In some representative embodiments, the composition may include microparticles having an average diameter of about 10 to about 110 microns and, in other embodiments, from about 25 to about 200 microns and from about 53 to about 106 microns. In various embodiments, the composition may include microparticles with an average diameter of about 53, about 60, about 70, about 80, about 90, and about 100 microns. In other embodiments, the composition may include microparticles having an average diameter of at least 50, at least 60, at least 70, at least 80, at least 90, at least 100, at least 200, at least 300, and at least 400 microns. In additional instances, the composition may include microparticles with a particle size distribution of about from about 53 to about 106 microns.

In some embodiments, microparticles having the diameters specified herein may have a relatively minimal effect on the surrounding tissues, i.e., the dura or thecal sac or nerve root sleeves. In many embodiments, microparticles of the desired size can be achieved using sieving. In some instances, the PMMA microparticles can be sieved into a fraction comprising microparticles with an average particle diameter of about 50 to about 100 microns. In additional instances, the PMMA microparticles can be sieved into a fraction comprising microparticles with an average particle diameter of 50 to 100 microns.

In one embodiment, the composition of the present disclosure comprises biocompatible microparticles including PMMA microparticles. In one instance, the PMMA microparticles may be non-linearly cross-linked.

Fully polymerized PMMA is histocompatible and can be incorporated in the human body without harmful toxic or carcinogenic reactions so that it can be considered as chemically and physically inert and biocompatible. PMMA is long lasting and does not degrade in the body. For these reasons, PMMA polymers have already been used for manufacturing implants such as bone cement for the plastic covering of bone defects in the face and in the cranium, or as in a total hip or total knee arthroplasty. PMMA is also being used for manufacturing artificial teeth, as artificial heart valves and for manufacturing intra-ocular lenses and dialysis membranes.

In another embodiment, the compositions of the present disclosure can include microparticles comprised of at least one of another biocompatible polymer including polyethylene, polypropylene, polystyrene, or cellulose acetate. In another embodiment, these compositions can include microparticles comprised of at least one of another biocompatible natural polymer including agarose, alginate, chitosan, polydextran, polystarch, starch, albumin, collagen, gelatin, calcium carbonate, lipids, tricalcium phosphate, and any other suitable polymer In another embodiment, these compositions can include microparticles comprised of at least one of another biocompatible polymer such as acrolein, glycidyl methacrylate, lactides, polyanhydride, polyiminocarbonates, and any other suitable polymer. In another embodiment, the compositions can include microparticles comprised of at least one of another biocompatible polymer such as glycolides, epoxy polymers, hygrogels, paraffin, pegylated poly(lactide), poly(lactide-co-glycolide), polyacrylates, polyacrylonitrile, polyamide, polyaminoacids, polycaprolactones, polyelectrolytes, polyester, polyphosphazenes, polyurea, and polyurethane. In some embodiments of the composition, the microparticles are small enough to be injected through a fine gauge cannula (e.g., 25 gauge) or an injection syringe to the desired spinal disc region.

In various embodiments, the compositions of the present disclosure may comprise, for example, about 30% about 60%, wherein % is g %, substantially smooth spherical PMMA microparticles ranging in size from about 25-about 125 microns in diameter. In certain embodiments, the composition percentage is calculated by weight. In other embodiments, the composition percentages may be calculated by volume. In some instances, the PMMA microparticles range in size from 25-125 microns in diameter. In various embodiments, the PMMA microparticles may have an average diameter size of about 25, about 30, about 40, about 50, about 60, about 70, about 80, about 90, about 100, and about 125 microns. In additional embodiments, the PMMA microparticles may have an average diameter size of at least 25, at least 30, at least 40, at least 50, at least 60, at least 70, at least 80, at least 90, and at least 100 microns. In one embodiment, the PMMA microparticles may range in size from about 53-106 microns in diameter. In some embodiments, the PMMA microparticles may range in size from about 53-about 106 microns in diameter. In various instances, the PMMA microparticles may range in size from 53-106 microns.

In various embodiments, the composition may comprise any suitable amount of PMMA microparticles without departing from the principles of this disclosure. In some instances, the composition may comprise about 50%-60%, wherein % is g %, of PMMA microparticles, ranging in size from about 53-106 microns in diameter. In various embodiments, the composition may comprise about 35-55% PMMA microparticles, ranging in size from about 53-106 microns in diameter. In various embodiments, the composition may comprise about 40-50% PMMA microparticles, ranging in size from about 53-106 microns in diameter. In various embodiments, the composition may comprise about 35-40% PMMA microparticles, ranging in size from about 53-106 microns in diameter.

In addition to the PMMA, the composition may comprise microparticles and at least an additive and PBS. PBS can act as a vehicle, a physiological buffer, and is compatible with physiological pH. In some embodiments, the additive may comprise Pluronic® surfactant and PBS. In various embodiments, the composition may comprise a solution of PMMA microparticles, Pluronic® surfactant, and PBS. In alternative embodiments, the additive may comprise hyaluronic acid (HA), carboxymethlycellulose (CMC), and/or polyvinyl alcohol (PVA). In yet another embodiment, the additive can be provided in a solution, solid, or dispersion form. In various embodiments the composition may comprise PMMA microparticles, a solution of Pluronic® surfactant, PBS and/or an amount of radiopaque particles or dye.

In various embodiments, the composition comprises about 8-25% of the additive. In certain embodiments, the composition comprises about 20-25% of the additive. In further embodiments, the composition comprises about 8-12% of the additive. In additional embodiments, the composition comprises 8-12% of the additive. In certain embodiments, the composition comprises about 8-10% of the additive.

In various embodiments, the composition may comprise Pluronic® surfactant as a viscosity enhancer. Pluronic® surfactant is a water soluble, non-ionic surfactant. Pluronic® surfactant can also be described as Pluronic®. Pluronic® can also be described as poloxamer. Pluronic® surfactant can also be described as Pluronic® excipient. One example of Pluronic® surfactant is poloxamer 407 (also known as Pluronic® F-127), which is a triblock copolymer composed of a hydrophobic residue of polyoxypropylene (POP) flanked by two hydrophilic units of polyoxyethylene (POE).

In various embodiments, the composition comprises about 8-25% of Pluronic® surfactant. In some embodiments, the composition comprises about 20-25% of Pluronic® surfactant. In certain embodiments, the composition comprises about 8-12% Pluronic® surfactant. In additional embodiments, the composition comprises 8-12% Pluronic® surfactant. In certain embodiments, the composition comprises about 8-10% Pluronic® surfactant. In another embodiment, the composition comprises 8-10% Pluronic® surfactant. In some embodiments, the composition may comprise at least 8%, at least 9%, and at least 10% Pluronic® surfactant.

In various embodiments the Pluronic® surfactant may have a molecular weight of about 10-about 14.6 kilodaltons (kDa). In some embodiments the Pluronic® surfactant may have a molecular weight of 10-14.6 kDa. In various embodiments the Pluronic® surfactant may be Pluronic® F-127. In yet another embodiment, the Pluronic® surfactant may be any form of Pluronic® surfactant.

In various embodiments, the composition comprises PMMA microparticles, PBS, Pluronic® surfactant, and the addition of a radio marker. The radio marker may be comprised of a contrast agent, chromophore, radiopaque dye, or other suitable material to allow better targeting of injection of the composition within the intervertebral disc (IVD). In some instances, the Pluronic® surfactant may facilitate the solubilization of the radio marker comprising a contrast agent or radiopaque dye.

In various embodiments, the contrast agent, can comprise one or more of sodium diatrizoate hydrate, barium sulfate, iodinated contrast media, and gadolinium. In various embodiments the radiopaque dye can comprise one or more of iohexol, iopamidol, and metrizamide. The composition can comprise about 9-about 15% of the radio marker and in certain instances about 10.7% of the radio marker. In yet another instance, the composition can comprise 9-15% of the radio marker. In yet another instance, the composition can comprise about 9-about 10% of the radio marker. In yet another instance, the composition can comprise 9-10% of the radio marker.

In certain embodiments the composition can comprise the radio marker comprising sodium diatrizoate hydrate. Sodium diatrizoate in the composition may act as a contrast agent for radiological imaging. The composition can comprise about 9-about 15% sodium diatrizoate hydrate and in certain instances about 10.7% sodium diatrizoate hydrate. In yet another instance, the composition can comprise 9-15% of sodium diatrizoate hydrate. In yet another instance, the composition can comprise about 9-about 10% of sodium diatrizoate hydrate. In yet another instance, the composition can comprise 9-10% of sodium diatrizoate hydrate.

In some embodiments, the composition may include microparticles that may result in radiopaque structures. In various embodiments microparticles that incorporate at least one of the following monomers, for example, will result in radiopaque structures: 2-[4'-iodobenzoyloxy]ethyl methacrylate and 2-[2',3',5'-triiodobenzoyloxy]ethyl methacrylate.

In certain embodiments, the composition can comprise at least one of polyethylene glycol (PEG) with a molecular weight of about 1 Dalton (Da)-8 kDa, polysorbate 80 (Tween80), glycerol, or carboxymethlycellulose (CMC). In some embodiments, the composition comprises about 5-about 15% PEG. In additional embodiments, the composition comprises 5-15% PEG. In various embodiments, PEG may be used to reduce extrusion force of the composition. In one or more embodiments, the composition comprises about 30-about 60% PMMA microparticles, about 2-about 3% CMC, and about 15-about 50% PBS. In some embodiments, the composition comprises about 30-about 60% PMMA microparticles, about 2-about 3% CMC, about 15-about 50% PBS, and about 9-about 15% sodium diatrizoate hydrate.

In some embodiments, the compositions as described herein may be comprised as a liquid form at 3-8 degrees° C. and comprised as a gel at human body temperature. In various embodiments, the compositions comprising Pluronic® surfactant may be comprised as a liquid at 3-8 degrees° C. and comprised as a gel at human body temperature. In various embodiments comprising CMC, the composition is comprised as a gel suspension at 3-8° C. and comprised as a gel at human body temperature. Some instances of the compositions may be designed to increase in viscosity upon exposure to a body temperature. In other instances, the compositions may be formulated as a non-gel form prior to injection and, after injection into the IVD, transition to a gel.

Compositions existing as a liquid at 3-8° C. and as a gel at human body temperature may be advantageous due to their ability to be injected into the IVD, allowed to set to a gel form, and wherein the composition as a gel form does not leak from the spinal disk or annulus pulposus.

As will be understood, not all compositions have the advantages discussed herein, nor do all compositions have the desired therapeutic effects.

In various embodiments, compositions including PMMA microparticles and Pluronic® surfactant results in an extrudable composition from 16-22-gauge needles, and 1.6, 6 inch, and 8 inch spinal needles. In various embodiments, compositions including PMMA microparticles and Pluronic® surfactant can achieve the desired liquid-gel properties of the composition wherein use of Pluronic® surfactant is superior to use of other additives.

In some embodiments, the composition comprises about 35-55% poly PMMA microparticles; about 8-25% Pluronic® surfactant; about 19-49% PBS; and about 8-14% of the radio marker, wherein the PMMA microparticles have a particle size distribution between about 53-106 microns and are nonlinearly cross-linked. In additional embodiments, the composition comprises 35-55% PMMA microparticles; 8-25% Pluronic® surfactant; 19-49% PBS; and 8-14% of the radio marker, wherein the PMMA microparticles have a particle size distribution between 53-106 microns and are nonlinearly cross-linked.

In additional embodiments, the composition comprises about 35-55% PMMA microparticles; about 8-25% Pluronic® surfactant; about 19-49% PBS; and about 8-14% sodium diatrizoate hydrate, wherein the PMMA microparticles have a particle size distribution between about 53-106 microns and are nonlinearly cross-linked. In additional embodiments, the composition comprises 35-55% PMMA microparticles; 8-25% Pluronic® surfactant; 19-49% PBS; and 8-14% sodium diatrizoate hydrate, wherein the PMMA microparticles have a particle size distribution between 53-106 microns and are nonlinearly cross-linked.

In various embodiments, the composition comprises about 45-55% PMMA microparticles; about 8-12% Pluronic® surfactant; about 19-49% PBS; and about 8-14% sodium diatrizoate hydrate, wherein the PMMA microparticles have a particle size distribution between about 53-106 microns and are nonlinearly cross-linked. In additional embodiments, the composition comprises 45-55% PMMA microparticles; 8-12% Pluronic® surfactant; 19-49% PBS; and 8-14% sodium diatrizoate hydrate, wherein the PMMA microparticles have a particle size distribution between 53-106 microns and are nonlinearly cross-linked.

In certain instances, the composition comprises about 35-40% PMMA microparticles; about 8-10% Pluronic® surfactant; about 42-45% PBS; and about 9-12% sodium diatrizoate hydrate, wherein the PMMA microparticles have a particle size distribution between about 53-106 microns and are nonlinearly cross-linked. In additional embodiments the composition comprises 35-40% PMMA microparticles; 8-10% Pluronic® surfactant; 42-45% PBS; and 9-12% sodium diatrizoate hydrate, wherein the PMMA microparticles have a particle size distribution between 53-106 microns and are nonlinearly cross-linked.

Previously developed compositions for treating a damaged spinal disc include a composition comprising a plurality of PMMA microparticles and hyaluronic acid as described in U.S. Pat. No. 10,806,825 incorporated by reference herein. Ease of injection, and lack of leaking from the IVD are necessary for proper administration of the composition for treatment of spinal disc. One advantage of the compositions described herein—including PMMA microparticles and Pluronic® surfactant—is that the composition comprises a transitional physical property wherein the composition is a liquid at a low temperature and a gel at body temperature. Body temperature can be defined as human or mammalian body temperature. Body temperature can include a body temperature of about between 97° F. (36.1° C.) and 99° F. (37.2° C.). The compositions comprising PMMA microparticles and Pluronic® surfactant may have a low viscosity at a low temperature (e.g., room temp or under refrigeration, 3-8° C.) which allows for the composition to be extrudable into the IVD. Furthermore, the compositions described herein may transition from a liquid to a gel as they warm to body temperature. This transitional physical property allows the composition to be easily extruded into the IVD wherein the needle is left in for a short time to allow for gelation to occur, and then the needle is removed.

Another advantage of the composition comprising PMMA microparticles and Pluronic® surfactant is that the composition may provide immediate bulking within the IVD, thereby leading to decreased nerve pain. In some embodiments the composition should be ensured to be homogenous prior to injection, with no settling of PMMA in the syringe.

In various embodiments, the composition of has a time to gelation of about 30 seconds to about 20 minutes. Time to gelation may be defined as the time it takes for the initially liquid composition to convert to a gel within the IVD at body temperature. In additional embodiments, the composition of has a time to gelation of about 2 to about 15 minutes. In additional embodiments, the composition of has a time to gelation of about 2 to about 10 minutes. In additional embodiments, the composition of has a time to gelation of about 3 to about 5 minutes. In various embodiments, the composition of has a time to gelation of 30 seconds to 20 minutes. In additional embodiments, the composition of has a time to gelation of 2 to 10 minutes. In additional embodiments, the composition of has a time to gelation of 2 to 15 minutes. In additional embodiments, the composition of has a time to gelation of 3 to 5 minutes. In yet other embodiments, the composition of has a time to gelation of at least 30 seconds, at least 2 minutes, at least 3 minutes, at least 5 minutes, at least 10 minutes, at least 15 minutes, and at least 20 minutes.

In various embodiments, the described composition comprising PMMA microparticles, PBS, Pluronic® surfactant, and the radio marker comprises a longer shelf life and greater stability compared to previous agents using PMMA microparticles and hyaluronic acid. Previously developed agents comprising a plurality of PMMA microparticles and hyaluronic acid can only be stored without deterioration for 2 years at 2-8° C. and 6 months at 20-25° C., whereas in various embodiments of the disclosure, the compositions comprising PMMA microparticles, PBS, Pluronic® surfactant, and the radio marker can be stored without deterioration for about 5 years or more at room temperature. In some embodiments of the disclosure, the composition has less endotoxin prior to sterilization since Pluronic® surfactant is synthetically produced as compared to other reagents that are processed and extracted from recombinant bacteria such as hyaluronic acid.

In some instances, the compositions may have a pre-injection viscosity of about 68400 cP to about 72000 cP when measured a method using a LV4 spindle, speed at 0.5 RPM, and a temperature of 6° C. Alternative measurements of viscosity could include measurement using a bulk sample (>10 g) using T-bar spindle with the Helipad system. Bulk samples of each formulation can be tested for viscosity data along with samples in syringes. Further viscosity measurements can be included wherein the viscosity is measured on the undisturbed sample or of the sample after mixing it with a spatula (e.g., if the composition separates into phases).

Exemplary Methods of Making

Various embodiments of the disclosure contain a method comprising: producing a carrier solution by mixing PBS, Pluronic® surfactant, and a radio marker in water; producing a composition by mixing a plurality of PMMA microparticles into the carrier solution, chilling and adding the therapeutic to a syringe vial; packaging the syringe vial in a pouch; sterilizing the syringe vial via terminal sterilization; and storing the sterilized syringe vial at about 3-8° C.

Turning to FIG. 1, one embodiment of a process 100 for making the compositions described herein is provided. The method 100 may include various phases. The process 100 may include a mixing water phase 102, followed by a mixing PMMA phase 104, followed by a bottling phase 106, followed by a pouching/packaging phase 108, followed by a sterilization phase 110, followed by a storage phase 112, and followed by a testing and inspection phase 114.

In some embodiments the mixing water phase 102 may include producing a carrier solution by mixing PBS, Pluronic® surfactant, and a radio marker in water for injection (WFI). In some instances, the Pluronic® is Pluronic® F127 and/or the radio marker may be sodium diatrizoate hydrate.

In some embodiments the mixing PMMA phase 104 may include mixing a plurality of PMMA microparticles into the carrier solution which results in the compositions of this disclosure. In some embodiments, during the mixing PMMA phase 104, the PMMA microparticles may be mixed into the carrier solution via a SpeedMixer at room temperature at about 2000 rpm for about 2 minutes and about 3 cycles. In some embodiments of phase 104, nonlinearly cross-linked PMMA microparticles with a particle size distribution of about 53-106 microns are mixed into the carrier solution. In additional embodiments of mixing PMMA phase 104, nonlinearly cross-linked PMMA microparticles with a particle size distribution of 53-106 microns are mixed into the carrier solution. In various embodiments, PMMA microparticles of a desired size can be achieved using sieving. In some instances, the PMMA microparticles can be sieved into a fraction comprising microparticles with an average particle diameter of about 50 to about 100 microns. In additional instances, the PMMA microparticles can be sieved into a fraction comprising microparticles with an average particle diameter of 50 to 100 microns.

In some embodiments the bottling phase 106 may include adding the resulting liquid composition to a vial and inserting a stopper, cap, and crimp. In some instances, the bottling phase 106 may include the steps of chilling the composition and adding the composition to a vial which is a syringe vial. In additional embodiments, the bottling phase 106 may include one or more of the steps of inserting a stopper, cap, and crimp into the syringe vial. In some instances, bottling phase 106 may include ensuring the composition is a liquid form. In additional embodiments, bottling phase 106 includes filling vials with about 5 cc of the composition.

In various embodiments the pouching/packaging phase 108 may include packaging the vials of the compositions in autoclave pouches. In yet another embodiment of pouching/packaging phase 108, the vials may be packaged in any suitable pouch or packaging for any type of sterilization. In various instances of pouching/packaging phase 108, any type of autoclave pouch can be used. In some instances, Tyvek® autoclave pouches may be used. In other instances of pouching/packaging phase 108, the vials may be packaged in any suitable pouch or packaging for e-beam sterilization. In various embodiments of pouching/packaging phase 108, the pouch or packaging can be used during autoclaving or for e-beam irradiation.

In some embodiments the sterilization phase 110 may include any suitable sterilization technique. In additional embodiments the sterilization phase 110 may include sterilization techniques comprising terminal sterilization. In yet another embodiment, the sterilization phase 110 may comprise sterilization including e-beam irradiation, gamma irradiation, or autoclaving. In additional embodiments, one advantage of the process 100 for making the composition is that the composition can be terminally sterilized as opposed to aseptic processing. In some instances, the sterilization phase 110 may include e-beam sterilization using a dosage of about 30-35 KGy. In additional instances, the phase 110 may include e-beam sterilization using a dosage of about 20-35 KGy.

In additional embodiments the storage phase 112 may include the step of storing the syringe vials of the composition at 3-5° C. In other instances, the storage phase 112 may include the step of storing the syringe vials of the composition at about 3-8° C.

In various embodiments the testing and inspection phase 114 may include testing and inspecting the final composition to determine the physical and biological properties. In at least one embodiment, at testing and inspection phase 114 the composition is homogenous prior to injection into a spinal disc.

In various embodiments, the method 100 may be used to prepare a composition including the various compositions as described in the disclosure. In additional embodiments, the method 100 may be used to prepare a composition comprised of about 35-55% PMMA microparticles; about 8-25% Pluronic® surfactant; about 19-49% PBS; and about 8-14% of the radio marker, wherein the PMMA microparticles have a particle size distribution between about 53-106 microns and are nonlinearly cross-linked. In further embodiments, the method 100 may be used to prepare a composition comprised of 35-55% PMMA microparticles; 8-25% Pluronic® surfactant; 19-49% PBS; and 8-14% of the radio marker, wherein the PMMA microparticles have a particle size distribution between 53-106 microns and are nonlinearly cross-linked.

In yet other embodiments, the method 100 may be used to prepare a composition comprised of about 35-55% PMMA microparticles; about 8-12% Pluronic® surfactant; about 19-49% PBS; and about 8-14% of the radio marker, wherein the PMMA microparticles have a particle size distribution between about 53-106 microns and are nonlinearly cross-linked. In further instances, the method 100 may be used to prepare a composition comprised of 35-55% PMMA microparticles; 8-12% Pluronic® surfactant; 19-49% PBS; and 8-14% of the radio marker, wherein the PMMA microparticles have a particle size distribution between 53-106 microns and are nonlinearly cross-linked. In some embodiments, the composition may be withdrawn into any suitable syringe or cannula. In various embodiments, the composition may be extruded using any suitable device.

Figure 2:
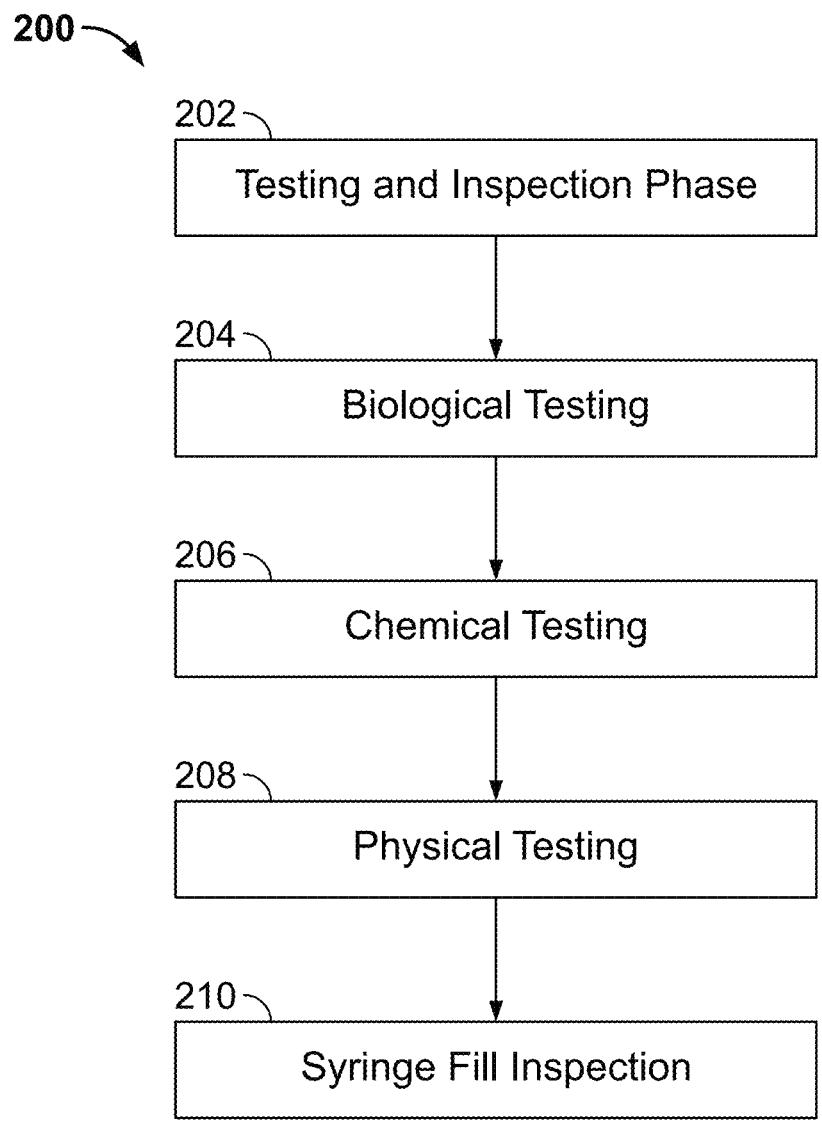
FIG. 2 is an exemplary process for inspecting a composition for treatment of discogenic pain, according to one embodiment.

Turning to FIG. 2, a method 200 for testing and inspection of the compositions of the disclosure is provided. The method 200 may include a testing and inspection phase 202 comprising a step 204 of biological testing, a step 206 of chemical testing, a step 208 of physical testing, and a step 201 of syringe fill inspection.

In various embodiments, biological testing 204 may include testing to determine presence of endotoxin. In additional embodiments, biological testing 204 could test for the presence of any biologically contaminant. In further instances, the biological testing 204 could test for the presence of any pathogen. In instances of biological testing 204, any suitable known methods in the art for endotoxin or pathogen testing may be used.

In additional embodiments, chemical testing 206 may include testing to determine the PMMA concentration in the composition. In some instances, the chemical testing 206 may comprise measurement of the pH of the composition. In instances of chemical testing 206, any known methods in the art for measuring PMMA concentration or pH may be used.

In some embodiments, physical testing 208 may include testing to determine the extrusion force required for the composition, testing to determine the elastic modulus of the composition, and/or testing for the viscosity of the composition. In instances of physical testing 208, any suitable known methods in the art for measuring extrusion force, elastic modulus, and viscosity may be used.

In additional embodiments, syringe fill inspection 210 may include inspecting the syringe vials for a correct fill value, wherein there is a substantially minimal air cap in the vial. In other instances, the vial may comprise no air gap. In further instances, syringe fill inspection 210 may include the steps of inspecting the syringe vials for lack of particle contamination, lack of cracking, lack of bubbles, lack of viscosity breakdown, and/or lack of vial defects. In some instances, syringe fill inspection 210 may include inspecting the vial for lack of bubbles wherein the bubbles are >1 mm. In various embodiments, extrusion testing may include extrusion force testing using 1 cc syringe filled with the composition wherein the composition is extruded through a 20-gauge spinal needle. The spinal needle may be 6 or 8 inches. In some instances, vial defects include cracking, malformations, and/or any other defect. Syringe fill inspection 210 may include any suitable method for measuring particle contamination. In certain embodiments, inspection may include a visual inspection performed after sifting. In at least one embodiment, at syringe fill inspection 210, the composition is homogenous prior to injection into a spinal disc.

Exemplary Methods of Use

In various embodiments, the composition comprising PMMA microparticles and Pluronic® surfactant can be injected into a spinal disc for the purpose of treating discogenic pain, spinal disc derangement, and annular welding or sealing of a spinal disc defect, such as a ruptured spinal disc. In some embodiments, the composition comprising PMMA microparticles and Pluronic® surfactant can be used for bulking or sealing anywhere in a human or other animal. In some embodiments, the composition can be used for bulking or sealing for leg, finger, spine, brain, or for dental applications. In yet another embodiment, the composition may be used outside the body for bulking or scaling.

In one embodiment, the composition of PMMA microparticles and Pluronic® surfactant is inserted into a central region of a ruptured spinal disc. Insertion of the composition into the ruptured spinal disc can attenuate a risk for recurrent spinal disc herniation and restore at least a portion of a structural integrity or shock absorbing capacity of the spinal disc. In various embodiments, once placed into the nucleus pulposus, the composition may mimic or provide a substitute for at least one characteristic of the physiologic structure of the spinal disc. For example, in some embodiments the composition may mimic the spinal disc and operate as a partial artificial disc or operate as a partial artificial nucleus pulposus. Accordingly, a morphology of a discogram may be improved following injection of the composition and impart physical stability to the interior of the spinal disc and/or to exterior portion of the annulus fibrosis. In certain embodiments, the composition can act as a sealant in the nucleus pulposus to prevent leakage. In various embodiments, the composition comprising PMMA microparticles and Pluronic® surfactant can beneficially increase spinal disc space height in proportion to the amount of the composition instilled which may vary from spinal disc to spinal disc.

In some embodiments, the composition comprising PMMA microparticles and Pluronic® surfactant can be injected into a spinal disc for treatment of discogenic pain wherein, after injection, a temperature of the spinal disc causes a temperature of the composition containing PMMA microparticles and Pluronic® surfactant to rise, thereby causing the Pluronic® surfactant to gel and provide a superior temporary bulking effect to the spinal disc compared to previous therapeutic compositions. In various embodiments, the method of treatment requires the composition to have a time to gelation of about 30 seconds to about 20 minutes. In some embodiments the method of treatment requires the composition to have a time to gelation of about 2 to about 15 minutes, or about 3 to about 5 minutes. In certain embodiments, the method of treatment requires the composition to have a time to gelation of 30 seconds to 20 minutes. In additional embodiments the method of treatment requires the composition to have a time to gelation of 2 to 15 minutes, or 3 to 5 minutes.

One embodiment includes a method of treating discogenic pain wherein the composition comprises PMMA microparticles wherein the composition after injection, a temperature of the spinal disc causes a temperature of the composition to rise, thereby causing the Pluronic® surfactant to gel and provide a beneficial temporary bulking effect to the spinal disc. In another embodiment, the composition comprises microparticles, for use in repairing and/or improving structural integrity of spinal discs, wherein after injection, a temperature of the spinal disc causes a temperature of the composition to rise, thereby causing the composition to gel and provide a beneficial temporary bulking effect to the spinal disc. In some embodiments, the method of treatment includes injecting a composition of PMMA microparticles, Pluronic® surfactant, and the addition of a radio marker including a contrast agent, chromophore, or radiopaque dye to allow better targeting of the composition within the IVD wherein and the Pluronic® surfactant may facilitate the solubilization of the radio marker including the contrast agent, chromophore, or radiopaque dye. In various embodiments, the contrast agent, can comprise one or more of sodium diatrizoate hydrate, barium sulfate, iodinated contrast media, gadolinium, or other suitable contrast agent. In various embodiments the radiopaque dye can comprise one or more of iohexol, iopamidol, metrizamide, or other suitable dye.

Various embodiments of the disclosure include a method of treating discogenic pain comprising inserting a needle into a nucleus pulposus of a spinal disc; injecting a composition into the nucleus pulposus of the spinal disc. In some embodiments, the composition comprises about 35-55% nonlinearly cross-linked PMMA microparticles with a particle size distribution of about 53-106 microns; Pluronic® surfactant PBS; and a radio marker. In further embodiments, after injection, a temperature of the spinal disc causes a temperature of the composition to rise, thereby causing the composition to gel and provide a beneficial temporary bulking effect to the spinal disc.

In some embodiments, a method of treating discogenic pain includes the steps of inserting a needle into a nucleus pulposus of a spinal disc; injecting the composition into the nucleus pulposus of the spinal disc. In some embodiments, the step of injecting comprises injecting the composition wherein the composition comprises about 35-55% nonlinearly cross-linked PMMA microparticles with a particle size distribution of about 53-106 microns; about 8-12% Pluronic® surfactant; about 19-49% PBS; and about 8-14% sodium diatrizoate hydrate. In additional embodiments, the method of treating discogenic pain includes after injection, a temperature of the spinal disc causes a temperature of the composition to rise, thereby causing the composition to gel and provide a beneficial temporary bulking effect to the spinal disc.

Some embodiments include a method of treating a discogenic pain comprising the steps of: inserting a needle into a nucleus pulposus of a spinal disc; injecting a composition into the nucleus pulposus of the spinal disc. In some embodiments, the step of injecting comprises injecting the composition wherein the composition comprises about 35-40% nonlinearly cross-linked PMMA microparticles with a particle size distribution of about 53-106 microns; about 8-10% Pluronic® surfactant; about 42-45% PBS; and about 9-12% sodium diatrizoate hydrate. In additional embodiments, the method of treating discogenic pain includes after injection, a temperature of the spinal disc causes a temperature of the composition to rise, thereby causing the composition to gel and provide a beneficial temporary bulking effect to the spinal disc.

Various embodiments include a method of treating discogenic pain comprising the steps of inserting a needle into a nucleus pulposus of a spinal disc; injecting a composition into the nucleus pulposus of the spinal disc, wherein: the composition comprises about 30-60% nonlinearly cross-linked poly (methyl methacrylate) (PMMA) microparticles with a particle size distribution of about 53-106 microns; about 2-about 3% CMC; about 40-70% PBS; and about 9-15% sodium diatrizoate hydrate; after injection, a temperature of the spinal disc causes a temperature of the composition to rise, thereby causing the Pluronic® surfactant to gel and provide a beneficial temporary bulking effect to the spinal disc.

Figure 3:
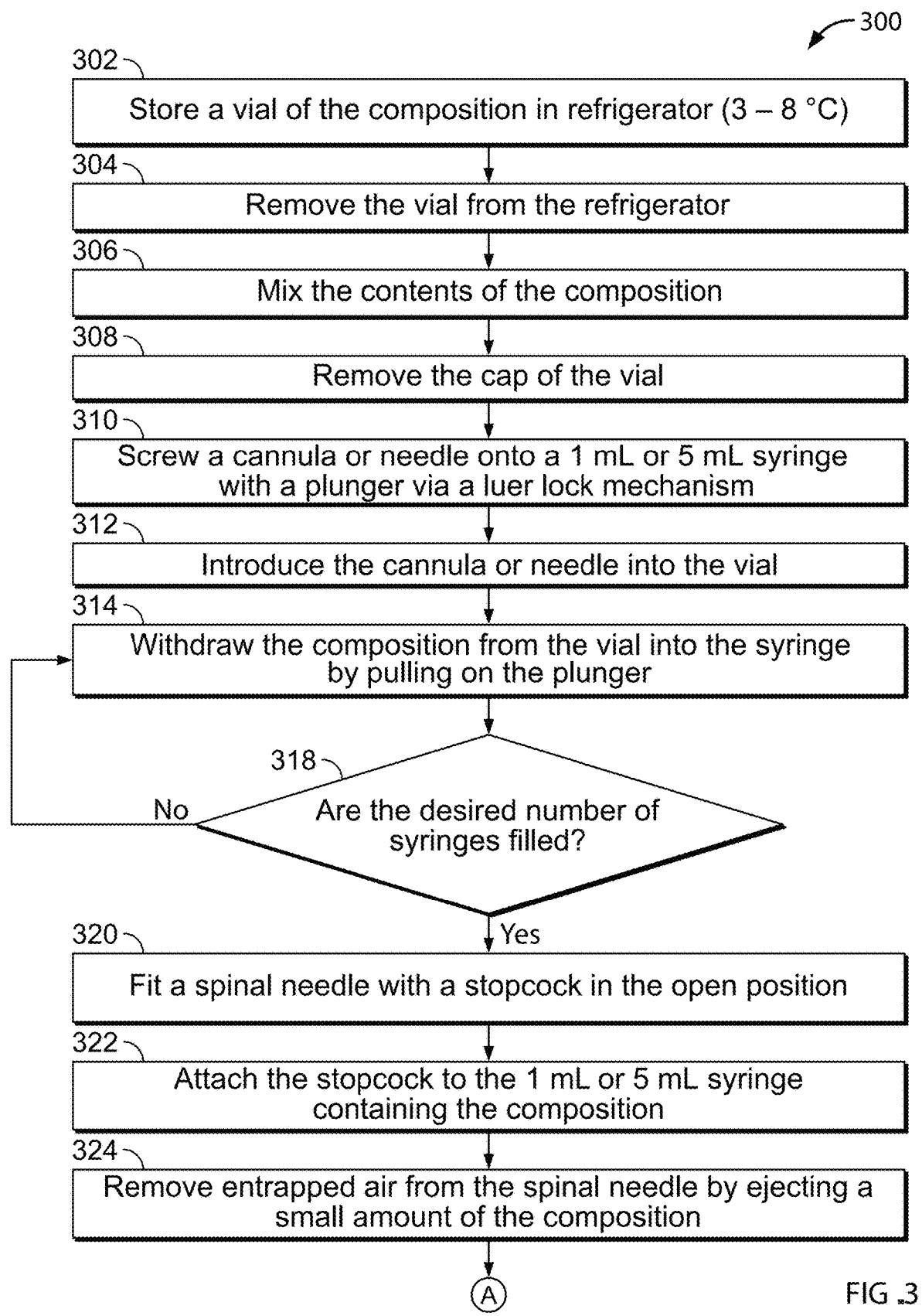
FIG. 3 is an exemplary method of use of a composition for treatment of discogenic pain, according to one embodiment.
Figure 3:
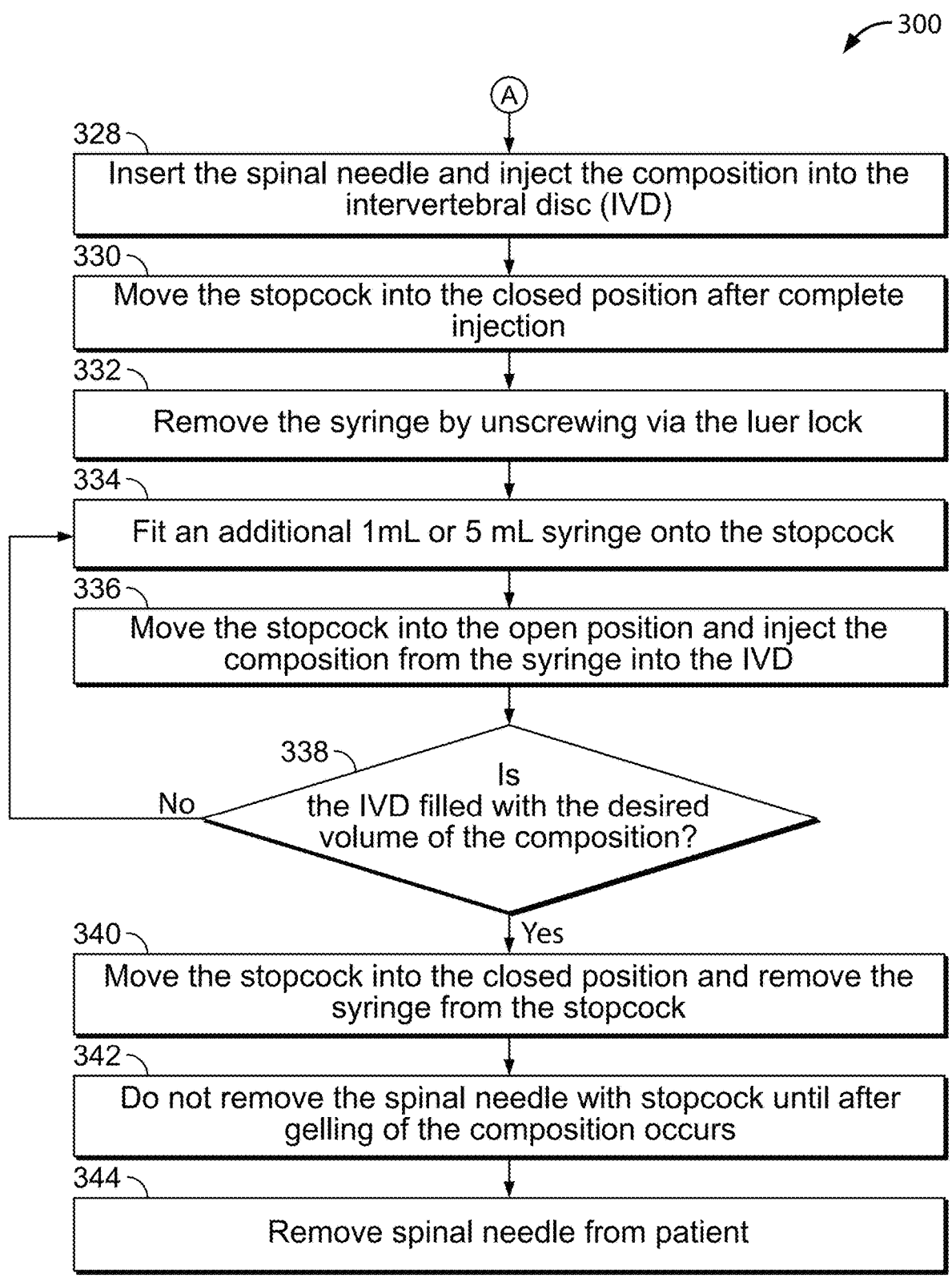

Turning to FIG. 3, an embodiment of a method 300 for treating discogenic pain is provided. The method 300 may include the following steps: store a vial of the composition in refrigerator (3-8° C.) 320, remove the vial from the refrigerator 304, shake the vial to mix the contents of the composition 306, remove the cap of the vial 308, screw a cannula onto a 1 ml syringe with a plunger via a luer lock mechanism 310, introduce the cannula into the vial 312, and withdraw the composition from the vial into the 1 mL syringe by pulling on the plunger 314.

The method 300 further includes a decision step 318 wherein if the desired number of syringes is not filled, step 314 is repeated. Once the desired number of syringes is filled, the method may continue to step 320. The method 300 further comprises the following steps: fit a spinal needle with a stopcock in the open position 320, attach the stopcock to the 1 mL syringe containing the composition 322, remove entrapped air from the spinal needle by ejecting a small amount of the composition 324, insert the spinal needle and inject the composition into the IVD 328, move the stopcock into the closed position after complete injection 330, remove the syringe by unscrewing via a luer lock 332, fit an additional 1 mL syringe onto the stopcock 334, and move the stopcock into the open position and inject the composition from the syringe into the IVD 336.

The method 300 further includes a decision step 338 wherein if the IVD is not filled with a desired volume of the composition, steps 334 and 336 are repeated. Once the desired number of syringes is filled, the person or machine performing method 300 may continue to step 340. The method 300 further comprises the following steps: move the stopcock into the closed position and remove the syringe from the stopcock 340, do not remove the spinal needle with stopcock until after gelling of the composition occurs 342, and remove spinal needle from the patient 344.

In some embodiments, the method 300 uses any suitable vial including, but not limited to, a syringe vial. In some instances, the spinal needle of method 300 can include any suitable spinal needle. In various embodiments the method 300 may use a 6-inch or 8-inch spinal needle. In additional embodiments of the method 300, a similar suitable device may be used instead of a cannula. In yet another instance, the vial cap of method 300 is a crimp cap.

In various embodiments, step 342 comprises allowing the syringe to remain in the patient until gelation of the composition occurs. In some instances, gelation of the composition may prevent back extrusion of the composition. Back extrusion is defined as substantial leaking of the composition out of the IVD. In some embodiments of the method 300, an amount of minimal back extrusion of the composition through the injection site may occur after injection without departing from the principles of this disclosure. In various instances back extrusion can be used as an indicator of functionality. In some embodiments the method 300 of treating spinal disk comprising administering the composition does not result in substantial back extrusion.

Figure 4:
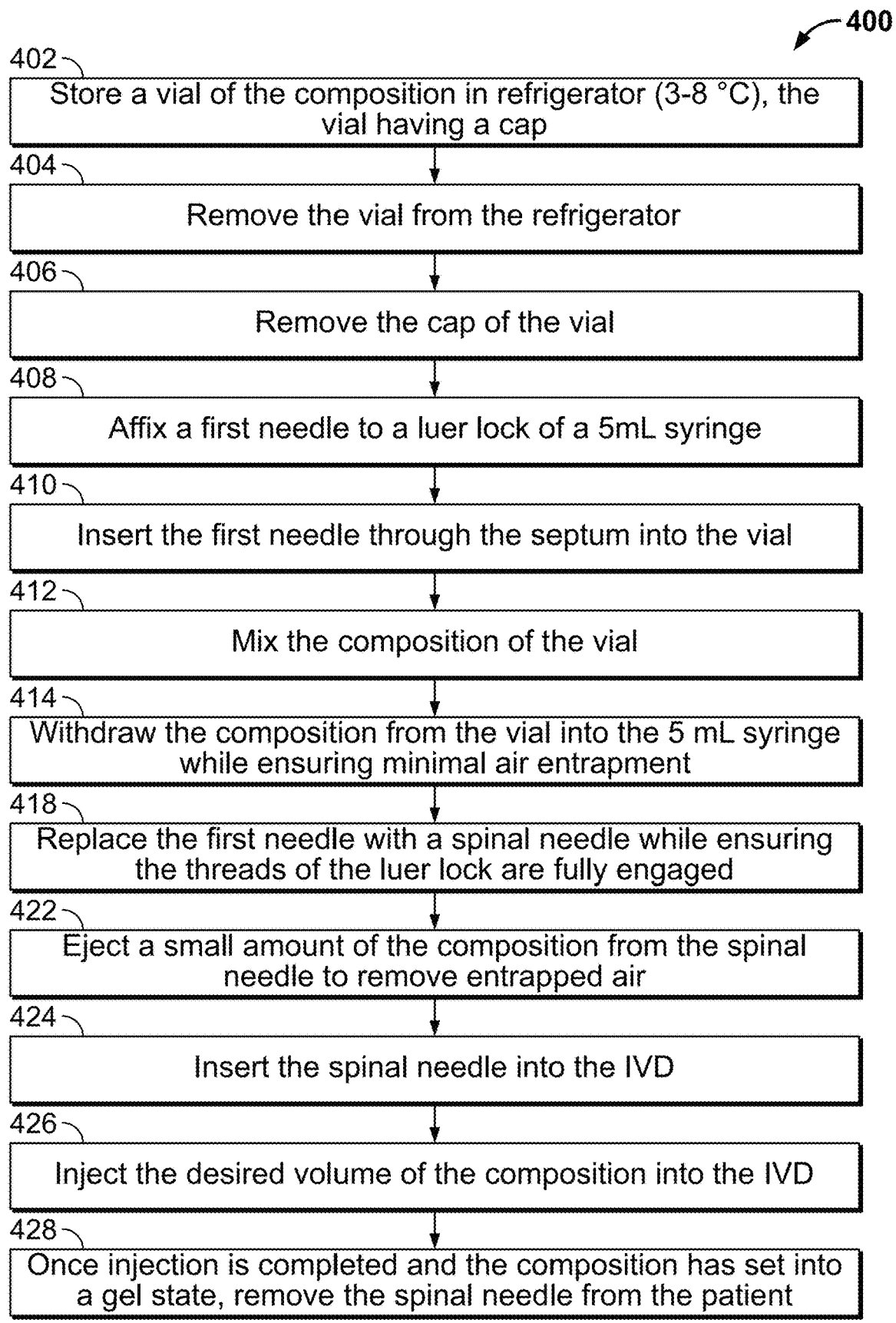
FIG. 4 is an exemplary method of use of a composition for treatment of discogenic pain, according to one embodiment.

Referring now to FIG. 4, an embodiment of a method 400 for treating discogenic pain is provided in accordance with the principles of this disclosure. Method 400 may include the following steps: store a vial of the composition in refrigerator (3-8° C.), the vial having a cap 402, remove the vial from the refrigerator 404, remove the cap of the vial 406, affix a first needle to a luer lock of a 5 ml syringe 408, insert the first needle through the septum into the vial 410, mix the composition of the vial 412, withdraw the composition from the vial into the 5 ml syringe while ensuring minimal air entrapment 414, replace the first needle with a spinal needle while ensuring the threads of the luer lock are fully engaged 418, eject a small amount of the composition from the spinal needle to remove entrapped air 422, insert the spinal needle into the IVD 242, inject the desired volume of the composition into the IVD 426, and once the injection is completed and the composition has set into a gel state, remove the spinal needle from the patient 428.

In some embodiments, the method 400 uses any suitable vial including a syringe vial. In some instances, the spinal needle of the method 400 can include any suitable spinal needle. In various embodiments the method 400 may use a 6-inch or 8-inch spinal needle. In yet another instance, the vial cap of method 400 is a crimp cap.

In some instances, step 412 comprises mixing via applying an angular motion so as to break up a PMMA layer in the composition resulting in a composition including a semi-homogeneous suspension. In alternative embodiments, step 412 comprises mixing via applying a back-and-forth motion using the syringe plunger resulting in a composition including a homogenous suspension.

In various embodiments, step 428 comprises allowing the syringe to remain in the patient until gelation of the composition occurs. In some instances, gelation of the composition may prevent back extrusion of the composition. In some embodiments of the method 400, an amount of minimal back extrusion of the composition through the injection site may occur after injection without departing from the principles of this disclosure. In various instances back extrusion can be used as an indicator of functionality. In various embodiments the method 400 of treating spinal disk comprising administering the composition does not result in substantial back extrusion.

In various embodiments, the methods 300, 400 of treatment require the composition to have a time to gelation of about 30 seconds to about 20 minutes. In some embodiments the methods 300, 400 of treatment require the composition to have a time to gelation of about 2 to about 15 minutes, or about 3 to about 5 minutes. In some embodiments, the methods 300, 400 of treatment require the composition to have a time to gelation of 30 seconds to 20 minutes. In additional embodiments the methods 300, 400 of treatment require the composition to have a time to gelation of 2 to 15 minutes, or 3 to 5 minutes.

In some embodiments the methods 300 and 400 may be used to inject compositions comprising the compositions as described above. In additional instances, the methods 300, 400 may be used to inject compositions comprising a composition comprised of about 35-55% PMMA microparticles; about 8-25% Pluronic® surfactant; about 19-49% PBS; and about 8-14% of the radio marker, wherein the PMMA microparticles have a particle size distribution between about 53-106 microns and are nonlinearly cross-linked. In further embodiments, the methods 300 and 400 may be used to inject compositions comprising 35-55% PMMA microparticles; 8-25% Pluronic® surfactant; 19-49% PBS; and 8-14% of the radio marker, wherein the PMMA microparticles have a particle size distribution between 53-106 microns and are nonlinearly cross-linked.

In further instances, the methods 300, 400 may be used to inject compositions comprising a composition comprised of about 35-55% PMMA microparticles; about 8-12% Pluronic® surfactant; about 19-49% PBS; and about 8-14% of the radio marker, wherein the PMMA microparticles have a particle size distribution between about 53-106 microns and are nonlinearly cross-linked. In further embodiments, the methods 300 and 400 may be used to inject compositions comprising 35-55% PMMA microparticles; 8-12% Pluronic® surfactant; 19-49% PBS; and 8-14% of the radio marker, wherein the PMMA microparticles have a particle size distribution between 53-106 microns and are nonlinearly cross-linked.

In some embodiments, a method of treating discogenic pain includes 1) injecting the composition into the nucleus pulposus of the spinal disc according to the methods 300 or 400 as a first injection; and 2) determining a pain level of the patient after the first injection; and 3) in response to determining that the pain level of the patient is above a particular threshold, injecting the composition into the nucleus pulposus of the spinal disc a second time.

In another embodiment, a medical kit comprises the composition comprising about 35-55% nonlinearly cross-linked PMMA microparticles with a particle size distribution of about 53-106 microns; about 8-12% Pluronic® surfactant; about 19-49% PBS; and about 8-14% sodium diatrizoate hydrate as well as surgical tools for administration. In another embodiment, a medical kit comprises the composition comprises about 35-40% nonlinearly cross-linked PMMA microparticles with a particle size distribution of about 53-106 microns; about 8-10% Pluronic® surfactant; about 42-45% PBS; and about 9-12% sodium diatrizoate hydrate; as well as surgical tools for administration. Such a kit may include a quantity of the composition, and a delivery device such as a syringe or other applicator, one or more surgical tools used in conventional spinal disc access and repair surgery are also advantageously provided in such kits.

In various embodiments, a medical kit comprises 6 ml vial containing 1. 6 ml vial containing 5.5 g of the composition comprising PMMA microparticles and Pluronic® surfactant, rubber septum with a crimped top, 20G 6-inch spinal needle, stopcock, luer lock with male & female connectors, five 1 ml graduated syringes, 18G 1.5" cannula, 18G 1.5" needle, or modified luer lock connector (this device is meant to withdraw contents from vial into 1 ml syringe). The above-described embodiments have been provided by way of example, and the present disclosure is not limited to these examples. Multiple variations and modifications to the disclosed embodiments will occur, to the extent not mutually exclusive, to those skilled in the art upon consideration of the foregoing description. Additionally, other combinations, omissions, substitutions, and modifications will be apparent to the skilled artisan in view of the disclosure herein. Accordingly, the present disclosure is not intended to be limited by the disclosed embodiments.

EXAMPLES

Example 1

In this Example, illustrative compositions are provided.

TABLE 1

| Concentration (g %), Range | Component | Description | Function |
|---|---|---|---|
| 35-55 | PMMA | PMMA microparticles, about 53-106 microns diameter PSD (particle size distribution), cross-linked (not linear) | Can provide bulking and volumizing within the IVD. PMMA is long lasting and does not degrade in the body. |
| 8-12 | Pluronic ® F127 | Also known as Poloxamer 407. | Can act as a delivery vehicle and/or a viscosity enhancer. Allows for the composition to gel at body temperature |
| 19-49 | PBS | Phosphate buffered saline | Physiological buffer. pH modification. |
| 8-14 | SDH | Sodium Diatriazoate Hydrate Water soluble sodium salt of an iodine compound. Active component in Hypaque (radiopaque diagnostic agent). | Can be used as a radio marker/contrast agent for radiological imaging. |

Additional Material Information
PMMA. PMMA, 11-145 micron PSD, sieved into 53-106 micron PSD fraction
Pluronic ® F127. Pluronic ® F-127 (Poloxamer 407), Ave MW = 10K-14.6K
PBS. Phosphate Buffered Saline
SDH. Sodium diatrizoate hydrate, >=98.0%

Example 2

In this Example, illustrative compositions are provided.

TABLE 2

| Concentration (g %), Nominal | ID | Description | Function |
|---|---|---|---|
| 35-40 | PMMA | PMMA microparticles, about 53-106 microns diameter PSD (particle size distribution), cross-linked (not linear) | Can provide bulking and volumizing within the IVD. PMMA is long lasting and does not degrade in the body. |
| 8-10 | Pluronic ® F127 | Also known as Poloxamer 407. | Can act as a delivery vehicle and/or a viscosity enhancer. Allows for the composition to gel at body temperature |
| 42-45 | PBS | Phosphate buffered saline | Physiological buffer. pH modification. |
| 9-12 | SDH | Sodium Diatriazoate Hydrate Water soluble sodium salt of an iodine compound. Active component in Hypaque (radiopaque diagnostic agent). | Can be used as a radio marker/contrast agent for radiological imaging. |

Additional Material Information
PMMA. PMMA (polymethyl methacrylate), 11-145 micron PSD diameter, sieved into 53-106 PSD micron fraction
Pluronic ® F127. Pluronic ® F-127 (Poloxamer 407), Ave MW = 10K-14.6K
PBS. Phosphate Buffered Saline
SDH. Sodium diatrizoate hydrate, >=98.0%

Example 3

In this Example, illustrative compositions are provided.

TABLE 3

Concentration of Components (g %) in Composition Formulations

| Composition No. | PMMA | Pluronic | Radio marker | PBS |
|---|---|---|---|---|
| 1 | 45 | 10 | 10 | 35 |
| 2 | 50 | 10 | 10 | 30 |
| 3 | 45 | 9 | 10 | 36 |
| 4 | 50 | 9 | 10 | 31 |
| 5 | 45 | 8.75 | 10 | 36.25 |
| 6 | 50 | 8.75 | 10 | 31.25 |
| 7 | 45 | 8 | 10 | 37 |
| 8 | 50 | 8 | 10 | 32 |

Example 4

In certain embodiments, the compositions as described herein have viscosity values of about 68400 cP to about 72000 cP. Viscosity was recorded every 10 seconds (cP) using the following experimental parameters: a LV4 spindle, speed at 0.5 RPM, temperature at 6° C. The sample amount included about 4 mL in a 5 mL glass vial. It was noted that viscosity decreases during measurement.

TABLE 4

Viscosity (cP) of exemplary composition with 50% PMMA

| | |
|---|---|
| Measurement 1 | 72000 |
| Measurement 2 | 70800 |
| Measurement 3 | 69600 |
| Measurement 4 | 68400 |
| Measurement 5 | 69600 |
| Measurement 6 | 68400 |
| Mean | 69800 |

CONCLUSION

The foregoing description of the exemplary embodiments has been presented only for the purposes of illustration and description is not intended to be exhaustive or to limit the compositions, systems, and methods herein to the precise forms disclosed. Many modifications and variations are possible considering the above teachings.

The embodiments were chosen and described in order to explain the principles of the technology discussed herein and their practical application to enable others skilled in the art to utilize the various embodiments and with various modifications as are suited to the particular use contemplated. Alternative embodiments will become apparent to those skilled in the art to which the present technologies pertain without departing from their spirit and scope.

What is claimed is:

1. A composition of matter comprising:
   about 30-60% poly (methyl methacrylate) (PMMA) microparticles;
   about 8-25% poloxamer surfactant;
   about 19-49% phosphate buffered saline (PBS); and
   about 8-14% of a radio marker, wherein the PMMA microparticles have a particle size distribution between about 25-125 microns and are nonlinearly cross-linked.

2. The composition of matter of claim 1, further comprising:
   about 35-55% PMMA; and
   about 8-12% poloxamer surfactant.

3. The composition of matter of claim 1, wherein the PMMA microparticles have a particle size distribution between about 53-106 microns and are nonlinearly cross-linked.

4. The composition of matter of claim 1, further comprising about 2-3% carboxymethylcellulose.

5. The composition of matter of claim 1, wherein the composition is a liquid at temperatures of about 3-8° C. and a gel at body temperature.

6. The composition of matter of claim 5, wherein the composition has a time to gelation from about 3-8° C. to body temperature of about 30 seconds to 20 minutes.

7. The composition of matter of claim 6, wherein the composition has a time to gelation from about 3-8° C. to body temperature of about 2 minutes to 15 minutes.

8. The composition of matter of claim 7, wherein the composition has a time to gelation from about 3-8° C. to body temperature of about 3 minutes to 5 minutes.

9. The composition of matter of claim 6, wherein the composition has a time to gelation from about 3-8° C. to body temperature of about 30 seconds to 5 minutes.

10. The composition of matter of claim 1, wherein the composition has a pre-injection viscosity of about 68400 cP to about 72000 cP.

11. A composition of matter comprising:
    about 30-60% poly (methyl methacrylate) (PMMA) microparticles;
    about 8-25% of a hydrogel;
    about 19-49% phosphate buffered saline (PBS); and
    about 8-14% of a radio marker, wherein the PMMA microparticles have a particle size distribution between about 25-125 microns and are nonlinearly cross-linked.

12. The composition of matter of claim 11, wherein the hydrogel comprises poloxamer surfactant.

13. The composition of matter of claim 12, further comprising:
    about 35-55% PMMA; and
    about 8-12% poloxamer surfactant.

14. The composition of matter of claim 13, wherein the PMMA microparticles have a particle size distribution between about 53-106 microns and are nonlinearly cross-linked.

15. A method of making a composition of matter, wherein the composition comprises about 8-25% poloxamer surfactant, about 19-49% PBS, about 8-14% of the radio marker, and about 30-60% PMMA microparticles, the method comprising the steps of:
    mixing PBS, poloxamer surfactant, and a radio marker to form a carrier solution;
    mixing a plurality of nonlinearly cross-linked PMMA microparticles, wherein the PMMA microparticles have a particle size distribution of about 25-125 microns, into the carrier solution;
    chilling the composition to about 3-8° C.;
    adding the composition to a vial;
    sealing the vial;
    sterilizing the vial; and
    storing the sterilized vial at about 3-8° C.

16. The method of claim 15, wherein the mixing of the PMMA microparticles is performed using a mixer at room temperature for about 2 minutes at about 2000 rpm.

17. The method of claim 15, wherein the mixing of the PMMA microparticles into the carrier solution occurs at about 20° C.

18. The method of claim 15, wherein the radio marker comprises radiopaque dye.

19. The method of treating discogenic pain according to claim 15, wherein:
- injecting the composition into the nucleus pulposus of the spinal disc is a first injection; and
- the method further comprises the steps of:
    - determining a pain level of the patient after the first injection; and
    - in response to determining that the pain level of the patient is above a particular threshold, injecting the therapeutic solution into the nucleus pulposus of the spinal disc a second time.

20. A method of treating discogenic pain comprising the steps of:
- storing, at about 3-8° C., a vial having a cap, wherein the vial contains a composition, the composition comprising:
    - about 30-60% poly (methyl methacrylate) (PMMA) microparticles;
    - about 8-25% hydrogel;
    - about 19-49% phosphate buffered saline (PBS); and
    - about 8-14% of a radio marker, wherein the PMMA microparticles have a particle size distribution between about 25-125 microns and are nonlinearly cross-linked;
- removing the vial from storage;
- mixing the composition;
- removing the cap from the vial;
- attaching a cannula onto a syringe, the syringe having a plunger;
- inserting the cannula into the vial;
- withdrawing the composition from the vial into the syringe;
- attaching a spinal needle to the syringe, the spinal needle including a stopcock, wherein the stopcock is in an open position when it is attached to the syringe;
- remove any entrapped air from the spinal needle by ejecting a small amount of the composition from the syringe through the spinal needle;
- inserting the spinal needle into an intervertebral disc of a patient;
- injecting the composition into the intervertebral disc of the patient;
- upon fully injecting the composition into the intervertebral disc of the patient, moving the stopcock to a closed position;
- removing the syringe from the stopcock;
- allowing the composition to transition from a liquid to a gel as the composition increases in temperature; and
- upon gelation of the composition within the intervertebral disc of the patient, remove the spinal needle from the patient.

21. The method of claim 20, wherein the hydrogel comprises poloxamer surfactant.

22. The method of claim 21, wherein the composition further comprises about 35-55% PMMA and about 8-12% poloxamer surfactant.

23. The method of claim 20, wherein the PMMA microparticles have a particle size distribution between about 53-106 microns and are nonlinearly cross-linked.

24. The method of claim 20, wherein the composition further comprises about 2-3% carboxymethylcellulose.

25. The method of claim 20, wherein the composition is a liquid at temperatures of about 3-8° C. and a gel at body temperature.

26. The method of claim 20, wherein the composition has a time to gelation from about 3-8° C. to body temperature of about 30 seconds to 20 minutes.

* * * * *